(12) United States Patent
Yeshurun et al.

(10) Patent No.: US 6,533,949 B1
(45) Date of Patent: Mar. 18, 2003

(54) MICRONEEDLE STRUCTURE AND PRODUCTION METHOD THEREFOR

(75) Inventors: Yehoshua Yeshurun, Haifa (IL); Meir Hefetz, Mitzpe Harashim (IL); Meint de Boer, Enschede (NL); J. W. Berenschot, Winterswijk (NL); J. G. E. Gardeniers, Hengelo (NL)

(73) Assignee: Nanopass Ltd., Haifa (IL)

( * ) Notice: Subject to any disclaimer, the term of this patent is extended or adjusted under 35 U.S.C. 154(b) by 137 days.

(21) Appl. No.: 09/677,175

(22) Filed: Oct. 2, 2000

(51) Int. Cl.⁷ .............................................. A61M 37/00
(52) U.S. Cl. ................................ 216/11; 216/2; 216/39; 216/57; 216/67; 216/99; 604/264; 604/273
(58) Field of Search ................................ 216/2, 11, 39, 216/57, 67, 99; 604/264, 273

(56) References Cited

U.S. PATENT DOCUMENTS

| 5,591,139 A | 1/1997 | Lin et al. ..................... 604/264 |
| 2002/0020688 A1 * | 9/2001 | Sherman et al. ................ 216/2 |

FOREIGN PATENT DOCUMENTS

| WO | 99/64580 | 10/1999 | ........... C12N/15/00 |
| WO | WO 01/49362 A1 * | 7/2001 | .......... A61M/37/00 |

OTHER PUBLICATIONS

Chun et al, "An Array of Hollow Microcapillaries for the Controlled Injection of Genetic Materials into Animal/Plant Cells", *MEMS 99*, Orlando, Fla, Jan. 1999, p. 406–411.

* cited by examiner

Primary Examiner—Allan Olsen
(74) Attorney, Agent, or Firm—Mark M. Friedman

(57) ABSTRACT

A method for processing a wafer to form a plurality of hollow microneedles projecting from a substrate includes forming, by use of a dry etching process, a number of groups of recessed features, each including at least one slot deployed to form an open shape having an included area and at least one hole located within the included area. The internal surfaces of the holes and the slots are then coated with a protective layer. An anisotropic wet etching process is then performed in such a manner as to remove material from outside the included areas while leaving a projecting feature within each of the included areas. The protective layer is then removed to reveal the microneedles.

11 Claims, 6 Drawing Sheets

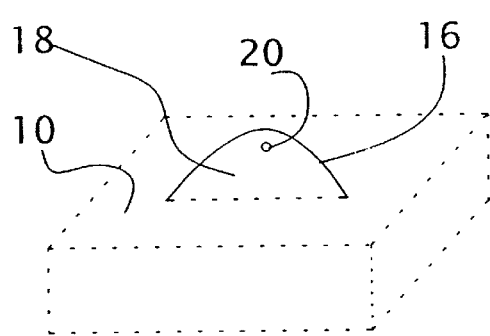
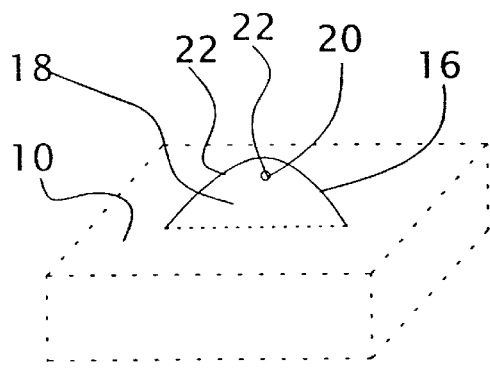
Fig. 1A  Fig. 1B
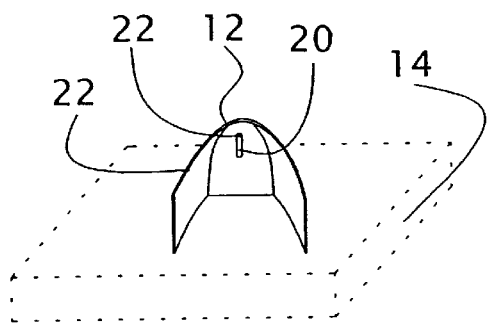
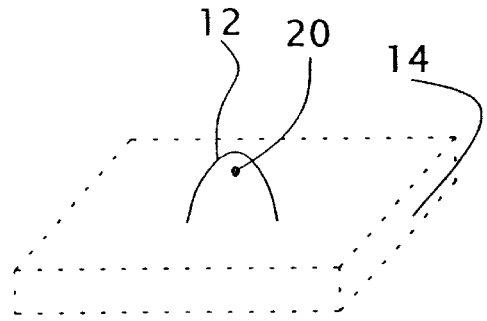
Fig. 1C  Fig. 1D

MICRONEEDLE STRUCTURE AND PRODUCTION METHOD THEREFOR

FIELD AND BACKGROUND OF THE INVENTION

The present invention relates to microneedle structures and, in particular, it concerns a microneedle production method and the microneedle structure produced thereby.

Much research has been directed towards the development of microneedles formed on chips or wafers by use of micro-machining techniques. This approach promises the possibility of producing numerous, very small needles which are sufficient to form small perforations in the dermal barrier, thereby overcoming the molecular size limitations of conventional transdermal patches, while being safe for use by unqualified personnel. Examples of such work may be found in PCT Publication No. WO 99/64580 to Georgia Tech Research Corp., as well as in the following scientific publications: "Micro machined needles for the transdermal delivery of drugs", S. H. S. Henry et al. (MEMS 98, Heildelberg, Germany, January 1998); "Three dimensional hollow micro needle and microtube arrays", D. V. McAllister et al. (Transducer 99, Sendai, Japan, June 1999); "An array of hollow micro-capillaries for the controlled injection of genetic materials into animal/plant cells", K. Chun et al. (MEMS 99, Orlando, Fla., January 1999); and "Injection of DNA into plant and animal tissues with micromechanical piercing structures", W. Trimmer et al. (IEEE workshop on MEMS, Amsterdam, January 1995). The more recent of these references, namely, the Georgia Tech application and the Chun et al. reference, disclose the use of hollow microneedles to provide a flow path for fluid flow through the skin barrier.

While hollow microneedles are potentially an effective structure for delivering fluids across the dermal barrier, the structures proposed to-date suffer from a number of drawbacks. Most notably, the proposed structures employ microneedles with flat hollow tips which tend to punch a round hole through the layers of skin. This punching action tends to cause damage to the skin. Additionally, the punched material tends to form a plug which at least partially obstructs the flow path through the microneedle. This is particularly problematic where withdrawal of fluids is required since the suction further exacerbates the plugging of the hollow tube within the microneedle. The flat ended form of the needles also presents a relatively large resistance to penetration of the skin, reducing the effectiveness of the structure.

A further group of proposed devices employ microneedles formed by in-plane production techniques. Examples of such devices are described in U.S. Pat. No. 5,591,139 to Lin et al., U.S. Pat. No. 5,801,057 to Smart et al., and U.S. Pat. No. 5,928,207 to Pisano et al. The use of in-plane production techniques opens up additional possibilities with regard to the microneedle tip configuration. This, however, is at the cost of very limited density of microneedles (either a single microneedle, or at most, a single row of needles), leading to corresponding severe fluid flow rate limitations. The very long proposed needle (about 3 mm) of Smart et al. suffers from an additional very high risk of needle breakage.

Co-pending U.S. patent application Ser. No. 09/589,369, which is unpublished at the date of filing this application and which does not constitute prior art, proposes an improved out-of-plane hollow microneedle structure having an aperture which is located behind a non-hollow piercing tip. The application describes a number of production techniques for such structures, including techniques based upon either dry etching or by combining wet etching techniques with asymmetric abrasion.

While the techniques described in the aforementioned co-pending application produce highly effective microneedle structures, various disadvantages are encountered while implementing such techniques in commercial production. Firstly, conventional deep reactive ion etching (DRIE) is generally sufficiently inaccurate to reduce the usable yield to unacceptably low proportions. Accuracy can be greatly improved by using cryogenic dry etching techniques. This option, however, greatly reduces the rate at which material can be etched away. As a result, these techniques are inefficient for processing large areas of a wafer. Wet techniques, on the other hand, are efficient for simultaneous processing of large regions of a wafer and offer high accuracy. Wet techniques are not, however, suited for directly achieving the asymmetrical forms required for implementation of the microneedles.

A further shortcoming of microneedle structures made by micromachining techniques is the brittleness of the resulting microneedles. Microneedles made from silicon or silicon dioxide are highly brittle. As a result, a significant proportion of the microneedles may fracture due to the stresses occurring during penetration, leaving fragments of the material within the tissue. Furthermore, oblique insertion by an unskilled person could lead to fracture of a very large proportion of the needles, resulting in malfunction of the device.

There is therefore a need for a method for producing hollow microneedles which would combine the advantages of dry and wet etching techniques to offer an effective and reliable production technique. It would also be highly advantageous to provide microneedle structures produced by such production methods.

SUMMARY OF THE INVENTION

The present invention is a method for producing hollow microneedles using a sequence of dry and wet etching techniques, and a hollow microneedle structure produced by such techniques.

According to the teachings of the present invention there is provided, a method for processing a wafer to form a plurality of hollow microneedles projecting from a substrate, the method comprising the steps of: (a) forming by use of a dry etching process a plurality of groups of recessed features, each group of recessed features including at least one slot deployed to form an open shape having an included area and at least one hole located within the included area; (b) coating internal surfaces of the holes and the slots with a protective layer; (c) performing an anisotropic wet etching process in such a manner as to remove material from outside the included areas while leaving a projecting feature within each of the included areas; and (d) removing the protective layer.

According to a further feature of the present invention, the open shape is substantially a V-shape formed from two substantially straight slots.

According to a further feature of the present invention, the V-shape is modified by a minimum radius of curvature at the intersection of the two substantially straight slots.

According to a further feature of the present invention, the two substantially straight slots subtend an angle of between about 60° and about 120° therebetween.

According to a further feature of the present invention, the two substantially straight slots subtend an angle of between about 85° and about 95° therebetween.

According to a further feature of the present invention, the dry etching process employs deep reactive ion etching.

According to a further feature of the present invention, the dry etching process includes cryogenic dry etching.

According to a further feature of the present invention, a minimum transverse dimension of the hole is greater than a minimum transverse dimension of the slots such that the hole extends to a depth greater than the slots.

According to a further feature of the present invention, a plurality of connecting holes are formed penetrating into a face of the wafer opposite to the projections such that the each of the connecting holes interconnects with a corresponding one of the holes to form a through channel for fluid flow.

According to a further feature of the present invention, the wet etching process employs a solution containing potassium hydroxide.

According to a further feature of the present invention, the wet etching process is performed in such a manner as to selectively remove material from within the included areas such that each of the projecting features exhibits an inclined upper surface sloping upward from the substrate.

There is also provided according to the teachings of the present invention, a microneedle structure integrally formed so as to project from a surface of a wafer, the surface corresponding substantially to a <100> crystallographic plane, the microneedle structure comprising: (a) at least one wall standing substantially perpendicular to the wafer surface; (b) an inclined surface corresponding to a crystallographic plane and extending from the wafer surface to an intersection with the at least one wall; and (c) a fluid flow channel extending from the inclined surface through to an opposing face of the wafer.

According to a further feature of the present invention, the at least one wall includes at least two substantially straight wall portions together forming a V-shape.

According to a further feature of the present invention, the at least one wall further includes a curved portion interconnecting the at least two substantially straight wall portions.

According to a further feature of the present invention, the two substantially straight wall portions subtend an angle of between about 60° and about 120° therebetween.

According to a further feature of the present invention, the two substantially straight wall portions subtend an angle of between about 85° and about 95° therebetween.

According to a further feature of the present invention, the inclined surface corresponds substantially to a <111> crystallographic plane.

BRIEF DESCRIPTION OF THE DRAWINGS

The invention is herein described, by way of example only, with reference to the accompanying drawings, wherein:

FIGS. 1A–1D are schematic isometric views illustrating four stages of a method for producing hollow microneedles according to the teachings of the present invention;

DESCRIPTION OF THE PREFERRED EMBODIMENTS

The present invention is a method for producing hollow microneedles using a sequence of dry and wet etching techniques, and a hollow microneedle structure produced by such techniques.

The principles and operation of production techniques and the resulting structures according to the present invention may be better understood with reference to the drawings and the accompanying description.

Turning now to the drawings, FIGS. 1A–1D and 2A–2F illustrate schematically a method for processing a wafer 10 to form a plurality of hollow microneedles 12 projecting from a substrate 14.

Figure 2A:
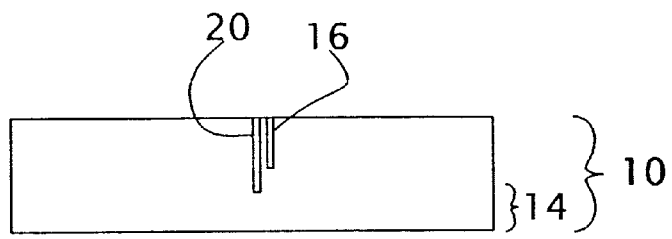
FIGS. 2A–2F are schematic cross-sectional views illustrating more fully the method of FIGS. 1A–1D.

Generally speaking, the method first employs a dry etching process to form a plurality of groups of recessed features, each group of recessed features including at least one slot 16 deployed to form an open shape having an included area 18 and at least one hole 20 located within included area 18. One such group of features is shown in FIGS. 1A and 2A.

Internal surfaces of holes 20 and slots 16 are then coated with a protective layer 22 (FIGS. 1B and 2D) prior to performing an anisotropic wet etching process to remove material substantially uniformly from outside included areas 18 while leaving a projecting feature, corresponding to microneedles 12, within each included area 18. This stage is shown in FIGS. 1C and 2E. Protective layer 22 is then removed, leaving microneedles 12 projecting from the surface of the substrate 14 (the remaining thickness of the initial wafer 10), as shown in FIGS. 1D and 2F.

It will be immediately appreciated that this process offers a highly efficient and reliable production technique for hollow microneedles. Specifically, since the volume of material to be removed by the dry etching process is small, highly accurate techniques, such as cryogenic DRIE, may be used to advantage without unduly lengthening the production time. The subsequent use of wet etching techniques then allows larger volumes of material to be removed quickly and accurately to achieve a high yield finished product. The structure of the resulting microneedles is highly robust and may be used to advantage for transdermal drug delivery and/or diagnostic sampling, for example, as part of the devices and systems described in the aforementioned U.S. patent application Ser. No. 09/589,369, which is hereby incorporated by reference. This and other advantageous of the method and corresponding structures of the present invention will be better understood from the following more detailed description.

Before turning to the features of the present invention in more detail, it will be helpful to clarify certain terminology as it is to be used throughout the description and claims. Firstly, the terms "dry etching process" and "wet etching process" are used according to their accepted usage to refer to etching processes in which the primary etching step is performed by exposure to a solution ("wet") or by other means ("dry"). Clearly, these terms do not exclude the use of additional preparatory or subsequent "dry" processing steps in a wet etching process, or vice versa.

The term "wafer" is used herein to refer to the material from which the microneedles are to be formed. Typically, the wafers used are single crystal wafers, most preferably of cubic structure such as silicon. The term "substrate" is used for the underlying structure upon which the microneedles are supported. Clearly, the substrate thus defined is generally a remaining thickness of the original wafer after completion of the processing.

The term "microneedle" is used herein to refer to a projection formed on a surface of a substrate. For transdermal fluid transfer applications, microneedles are configured to project to a maximum height above the substrate of no more than 2 mm, and typically no more than 500 μm. Further details of the design considerations in choosing dimensions of the microneedles for various applications are discussed in the aforementioned co-pending application and will not be dealt with here.

The term "hollow" is used to refer to a microneedle structure through which a fluid flow conduit passes, in contrast to a "solid microneedle" which lacks such a conduit. It should be noted that the conduit is typically a small proportion of the volume of the microneedle projection.

Finally, use will be made herein of various geometric terminology. Specifically, the term "open shape" is used to refer to a shape formed by one or more contiguous line which does not close on itself. Despite this lack of closure, reference is made to an "enclosed area" defined by the open shape. This enclosed area is defined to be the largest contiguous area which can be enclosed by adding a single straight line to the open shape. The open shape is chosen such that the enclosed area is non-zero, i.e., it is not a single straight line.

Turning now to the features of the present invention in more detail, the various stages of a preferred implementation of the production process will be described with reference to FIGS. 2A–2F.

Firstly, FIG. 2A shows wafer 10 after the dry etching process. Preferably, as mentioned above, high accuracy is achieved by using cryogenic DRIE or other high-accuracy dry etching processes. The wafer is first prepared, as is known in the art, by cleaning followed by lithography to prepare a mask for the DRIE. Preferably, a minimum transverse dimension of hole 20 is greater than a minimum transverse dimension of slots 16. As a result, hole 20 is etched at a slightly greater rate than slot 16, so that the hole extends to a greater depth. Typical values for the width of slots 16 are in the range of about 10 to about 20 microns. The dimensions of hole 20 are generally in the range of 20–150 micron, chosen as a function of the dimensions of the microneedles to be produced.

Figure 3A:
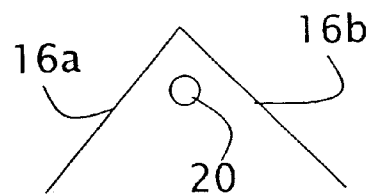
FIGS. 3A–3D are plan views of a number of alternative slot forms which may be used to implement the method of the present invention.
Figure 3B:
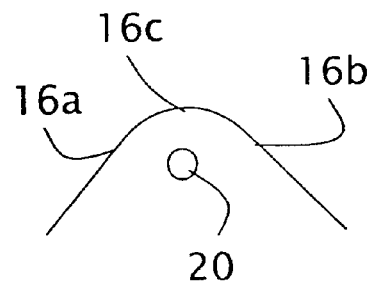

Referring briefly to FIGS. 3A–3D, it should be noted that a wide range of different configurations may be used for the open shape formed by slot(s) 16. In one preferred example shown in FIG. 3A, the open shape is a V-shape formed from two substantially straight slots 16a and 16b. FIG. 3B shows a more preferred example where the V-shape is modified by a curved connecting slot 16c having a given minimum radius of curvature at the intersection of the two substantially straight slots 16a and 16b. This minimum radius of curvature preferably has a value in the range of about 5 μm to about 100 μm, and most preferably in the range of 10–50 μm. The latter shape is believed to result in a more robust microneedle tip. In both cases, slots 16a and 16b preferably subtend an angle of between about 60° and about 120°, and more preferably between about 85° and about 95°, therebetween.

Figure 3C:
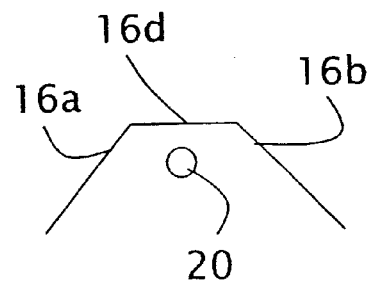
Figure 3D:
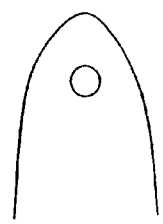

Although the aforementioned slot shapes are believed to be preferred, it should be noted that a wide range of other forms are also effective and may, in some cases, offer certain advantages. By way of example, FIG. 3C shows a slot configuration similar to FIG. 3B in which curved slot 16c is replaced by a third straight slot 16d. FIG. 3D shows a further example where the entire slot 16 is implemented as a single graduated curved form approximating to a U-shape.

It will be noted that the choice of open shape formed by slot(s) 16 and its orientation with respect to the crystal axes must be chosen in accordance with the intended wet etch process so as to form the required projecting microneedle. By way of example, in the case of the preferred KOH etch, the open shape must be sufficiently enclosed to inhibit the rapid etching of the <100> plane within the contained area, thereby allowing the required microneedle structure to form by etching of the <111> plane which occurs much more slowly in KOH. To form a symmetrical microneedle, the line that bisects the angle between slots 16a and 16b should be perpendicular to a <110> plane. In a most preferred example illustrated herein, the slots correspond substantially to two <100> planes.

The length dimensions of slot 16 are chosen according to the size of microneedle required.

Hole 20 also may vary in shape. In some cases, a circular hole may be preferred. An asymmetric hole, typically roughly elliptical, is often more advantageous, allowing an increase of the cross-section (and hence flow capacity) of the hole without coming overly close to slots 16. Optionally, other forms, such as a hole approximating to a triangular form, could be used to achieve similar results.

Figure 2B:
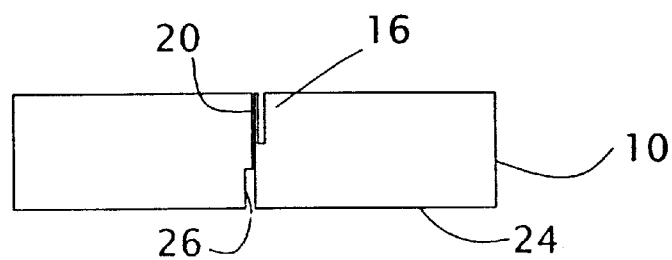

Turning now to FIG. 2B, it is a particularly preferred feature of the process and structure of the present invention that holes 20 are connected in fluid flow connection with the rear surface 24 of substrate 14 to allow fluid transfer via microneedles 12. To this end, a plurality of connecting holes 26 are preferably formed, penetrating into surface 24 such that each of connecting hole 26 interconnects with a corresponding hole 20 to form a through channel.

Connecting holes 26 are typically formed by back-side processing similar to that used for holes 20 and slots 16 on the front-side of the wafer. Precautions must be taken to ensure proper alignment of the front-side and back-side masks, as is known in the art. The tolerance of the alignment is preferably increased slightly by employing connecting holes 26 of diameter greater than the dimensions of front-side holes 20. The connecting holes are preferably centered slightly further away from slots 16 in order to avoid accidental perforation of the substrate via the slots. The depth differential between holes 20 and slots 16 provides an additional safeguard against this problem.

The order of processing of the front and back surfaces of the wafer is generally not critical, and depends primarily on practical logistical considerations. Thus, the back-side processing can be performed prior to any front-side processing, or between the dry and wet etching steps. Typically, however, the back-side processing should be performed prior to the wet etching step in order to avoid damage to the microneedles which are then formed on the front surface. Additionally, it may be advantageous to perform the front-side dry etch first to allow slight "over etching", i.e., etching to slightly greater than the theoretical required depth to ensure intersection with the back-side holes.

Figure 2C:
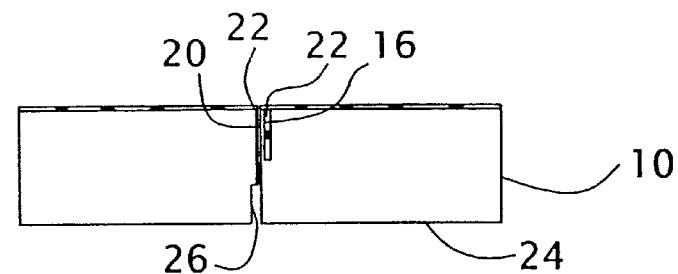
Figure 2D:
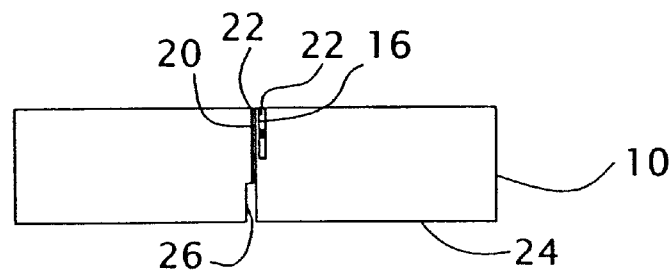
Figure 2E:
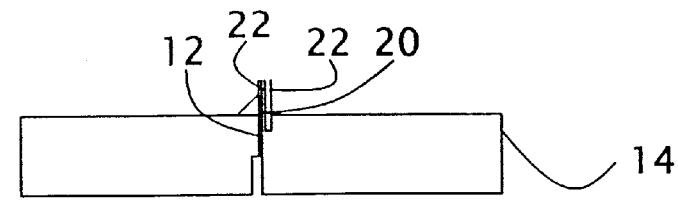
Figure 2F:
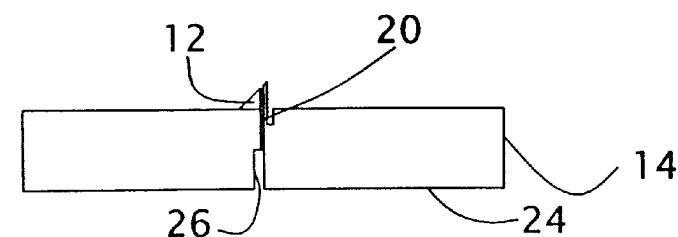

Turning now to FIGS. 2C, 2D and 2E, the choice of material for protective coating 22 must be suited to the type of wet etch process to be performed. In a particularly preferred implementation, the wet etching process employs a solution containing potassium hydroxide (KOH). A suitable protective coating material for such an implementation is SiRN. In order to achieve selective coating of the insides of holes 20 and slots 16, the coating is typically performed in two steps: first, a uniform coating over all exposed surfaces (FIG. 2C), such as by low pressure chemical vapor deposition (LPCVD); then, selective removal of the coating from the upper surface (FIG. 2D), such as by reactive ion etching (RIE), while leaving the coating within the holes and slots.

The anisotropic wet etching process then removes the upper surface of the wafer, generally keeping to the <100> horizontal crystallographic plane. Only where the etching process is asymmetrically limited by partial enclosure within walls formed by protective coating 22, the anisotropic wet etching process adopts alternative crystallographic forms, leading to formation of projections 12 (FIG. 2E). The protective coating 22 is then removed, typically by a further wet etching process. In the aforementioned example, the protective coating material is effectively removed by a hydrogen fluoride (HF) etch.

It will be noted that the pyramid-like structure of the microneedles produced by the method of the present invention is generally highly robust, thereby greatly reducing the likelihood of fracture during use of the microneedles. This robustness is further enhanced by the modification of the pyramid-like structure to include a rounded-wall configuration of FIGS. 1A–1D, 3B and 6. Nevertheless, in certain cases, the resulting structure may optionally be further processed by addition of various coating layers to provide additional desirable properties, as will now be described.

Firstly, depending upon the wafer material, it may be preferable to coat at least the microneedles with a layer of bio-compatible material, typically a metal or metal alloy. For this purpose, a coating of about 2 $\mu$m titanium or stainless steel is typically sufficient. Thicker coating of at least 10–20 $\mu$m may also serve a structural safety function, tending to prevent fragments being left behind in the event that a brittle silicon needle might fracture.

According to a further preferred option, a layer of at least about 20 $\mu$m of a super-elastic alloy is deposited over at least the conical projections. An example of such an alloy is the range of NiTi alloys generally known as Nitinol. This offers a still further enhanced level of structural safety by providing a layer which is not prone to breaking or fracturing under a very wide range of operating conditions.

One preferred technique for forming the aforementioned metallic layers is sputtering. Sputtering techniques for applying NiTi are discussed in "Micromachining Process for thin film SMA actuators", Nakamura et al. (IEEE, February 1996). In order to achieve the required NiTi stoichiometry to produce super elastic properties, it is recommended to use a target such as micro needles pre-coated with a small amount of Ti or Ni. Increasing or decreasing the amount of Ni or Ti or any ternary element can result in a film transformation which is the basic principle of super alloy properties of any desired composition. The exact composition defines the temperature at which the super elastic behavior is exhibited. It has also been demonstrated that adjusting the target to substrate distance and sputtering gas pressure can change the NiTi stoichiometry from 47% to 52% Ti, while using a 50% Ti target. Such changing in the stoichiometry could produce super elastic properties at about room temperature. The deposited amorphous films must be annealed to achieve crystallinity. This annealing also promotes adhesion to the substrate through formation of a thin reaction layer (~40 nm). For equi-atomic NiTi, no change of thin film phase transformation as observed when annealing between 500–700° C., However Ti-rich film displays an increased transformation temperature while Ni-rich film displays a decreased temperature transformation. Thin film can recover from 6% strain at 600 MPa forces which is above the need for microneedle configurations.

In yet a further option, at least part of the substrate material is removed by etching away from under the metallic or super-elastic layer so as to leave the microneedle projections formed substantially exclusively from the layer of metallic material or super-elastic alloy. In the most highly preferred case of a super-elastic alloy, this results in a microneedle array which is effectively unbreakable under a wide range of conditions. This provides a highly valuable solution to the problem of fractured microneedles associated with the prior art, and provides a greatly improved level of safety against damage to the device or harm to the user if the needles are inserted improperly at an oblique angle to the skin.

Although shown here schematically with a single microneedle, the process described is clearly well suited to producing a one- or two-dimensional arrays of microneedles projecting from the surface of substrate 12 with any desired spacing, layout and dimensions. In fact, it is a particularly preferred feature of the microneedle structures of the present invention that a two-dimensional array including at least 20 microneedles is provided. More preferably, at least 50 microneedles are provided on each chip, and most preferably, at least 100. In many practical applications, large arrays of several hundreds of microneedles may be formed on a chip of less than 1 cm$^2$. The spacing between centers of adjacent microneedles in a given direction is typically in the range of 2–10 times the maximum dimension of each needle in that direction.

Figure 4:
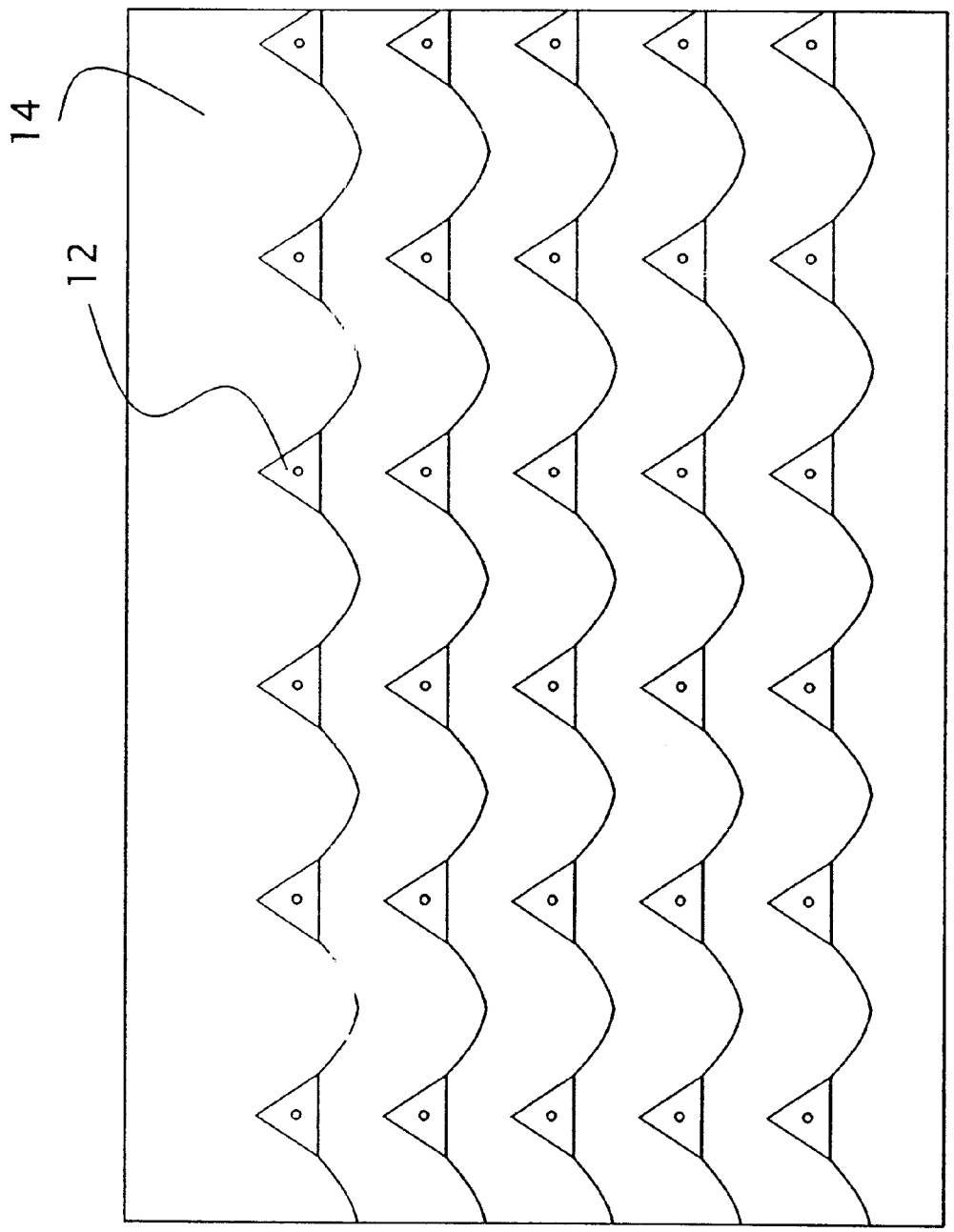
FIG. 4 is an enlarged isometric view of an array of hollow microneedles formed by the method of the present invention of a wafer surface.
Figure 5:
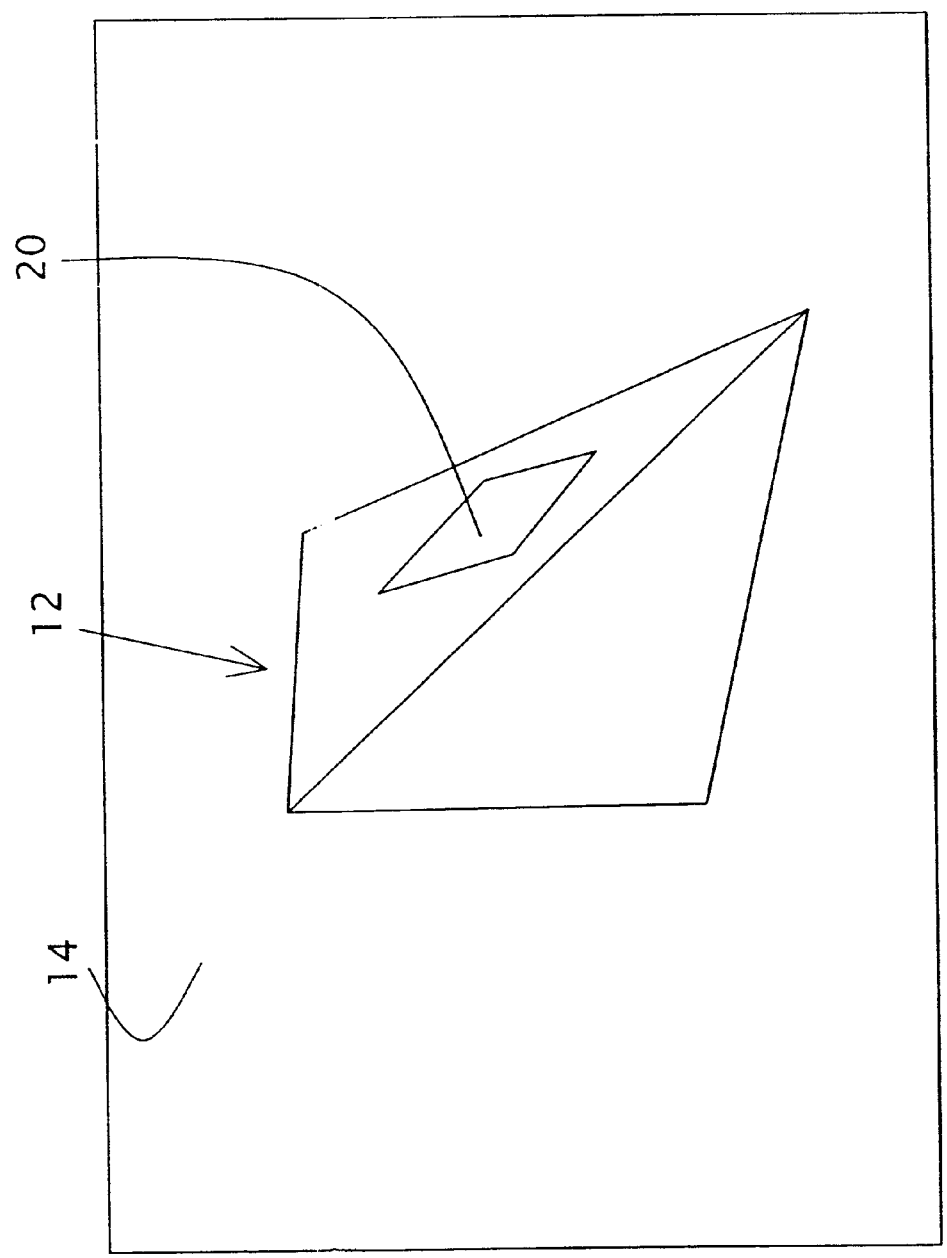
FIG. 5 is a further enlarged isometric view of one of the microneedles from FIG. 4.
Figure 6:
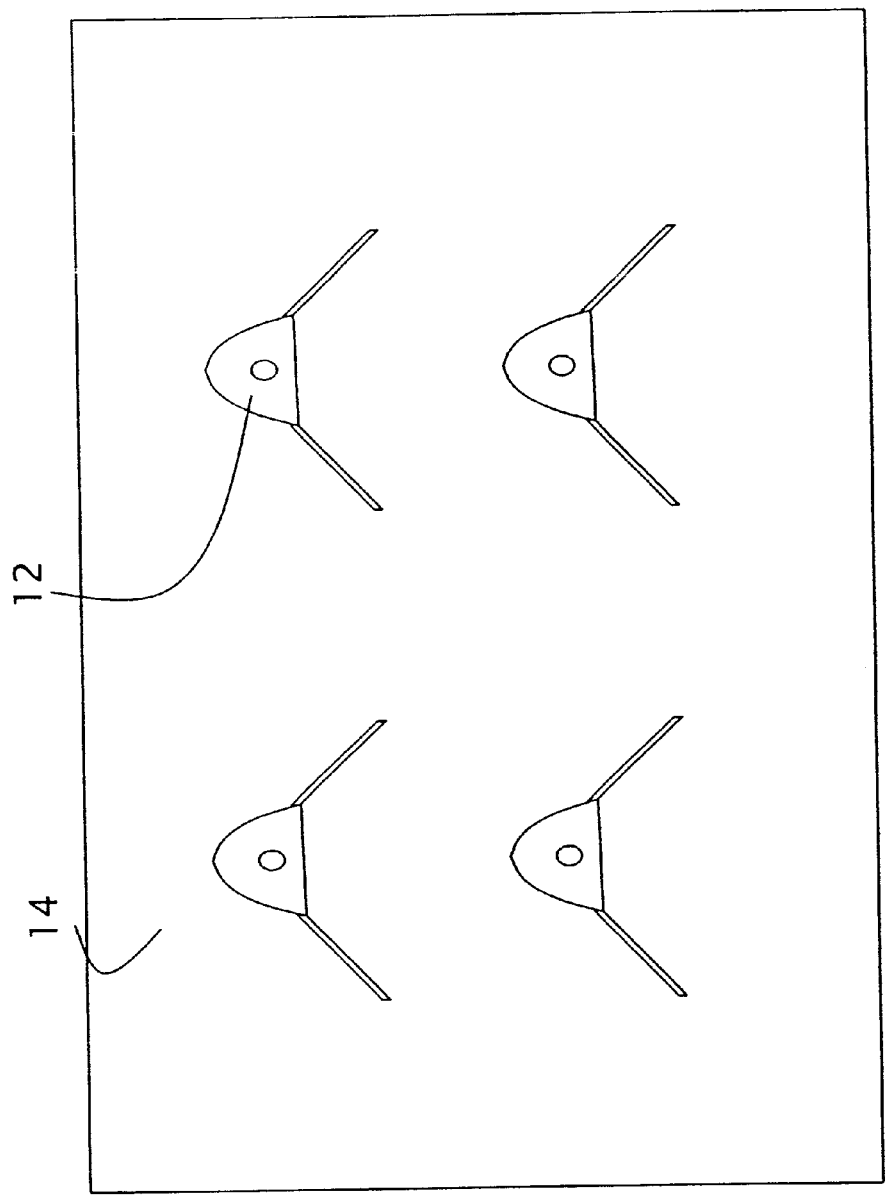
FIG. 6 is an enlarged isometric view of an array of a second form of hollow microneedles formed by the method of the present invention of a wafer surface.

Turning finally to FIGS. 4–6, these illustrate the microneedle structure resulting from the production process described above. Specifically, FIGS. 4 and 5 show an array of microneedles formed from the slot pattern of FIG. 3A, while FIG. 6 shows a corresponding array formed using the pattern of FIG. 3B.

In each case, the resulting structure includes an array of microneedles integrally formed so as to project from a wafer surface corresponding substantially to a <100> crystallographic plane. Each microneedle has at least one wall standing substantially perpendicular to the wafer surface, an inclined surface corresponding to a crystallographic plane and extending from the wafer surface to an intersection with the at least one wall, and a fluid flow channel extending from the inclined surface through to an opposing face of the wafer. The intersection of the fluid flow channel with the inclined surface offers an enlarged opening, thereby enhancing the capabilities of the microneedle for fluid transfer, and particularly diagnostic sample withdrawal, across a skin barrier.

In the preferred example described above employing KOH, the inclined surface corresponds substantially to a <111> crystallographic plane.

It will be appreciated that the above descriptions are intended only to serve as examples, and that many other embodiments are possible within the spirit and the scope of the present invention.

What is claimed is:

1. A method for processing a wafer to form a plurality of hollow microneedles projecting from a substrate, the method comprising the steps of:

(a) forming by use of a dry etching process a plurality of groups of recessed features, each group of recessed features including at least one slot deployed to form an open shape having an included area and at least one hole located within said included area;

(b) coating internal surfaces of said holes and said slots with a protective layer;

(c) performing an anisotropic wet etching process in such a manner as to remove material from outside said included areas while leaving a projecting feature within each of said included areas; and (d) removing said protective layer.

2. The method of claim 1, wherein said open shape is substantially a V-shape formed from two substantially straight slots.

3. The method of claim 2, wherein said V-shape is modified by a minimum radius of curvature at the intersection of said two substantially straight slots.

4. The method of claim 2, wherein said two substantially straight slots subtend an angle of between about 60° and about 120° therebetween.

5. The method of claim 2, wherein said two substantially straight slots subtend an angle of between about 85° and about 95° therebetween.

6. The method of claim 1, wherein said dry etching process employs deep reactive ion etching.

7. The method of claim 1, wherein said dry etching process includes cryogenic dry etching.

8. The method of claim 1, wherein a minimum transverse dimension of said hole is greater than a minimum transverse dimension of said slots such that said hole extends to a depth greater than said slots.

9. The method of claim 8, further comprising forming a plurality of connecting holes penetrating into a face of said wafer opposite to said projections such that said each of said connecting holes interconnects with a corresponding one of said holes to form a through channel for fluid flow.

10. The method of claim 1, wherein said wet etching process employs a solution containing potassium hydroxide.

11. The method of claim 1, wherein said wet etching process is performed in such a manner as to selectively remove material from within said included areas such that each of said projecting features exhibits an inclined upper surface sloping upward from said substrate.

* * * * *

UNITED STATES PATENT AND TRADEMARK OFFICE
CERTIFICATE OF CORRECTION

PATENT NO. : 6,533,949 B1
DATED : March 18, 2003
INVENTOR(S) : Yeshurun et al.

It is certified that error appears in the above-identified patent and that said Letters Patent is hereby corrected as shown below:

<u>Title page,</u>
Please insert Item:

-- [30]         Foreign Application Priority Data

28 August 2000      [IL]      Israel ............... 138131 --

Signed and Sealed this

Twenty-seventh Day of January, 2004

JON W. DUDAS
*Acting Director of the United States Patent and Trademark Office*